US005711985A

United States Patent [19]
Guerrero et al.

[11] Patent Number: 5,711,985
[45] Date of Patent: Jan. 27, 1998

[54] COMPOSITIONS TO ENHANCE TASTE OF SALT USED IN REDUCED AMOUNTS

[75] Inventors: Arturo Guerrero; Steven Soon-Young Kwon; Dharam Vir Vadehra, all of New Milford, Conn.

[73] Assignee: Nestec S.A., Vevey, Switzerland

[21] Appl. No.: 517,753

[22] Filed: Aug. 22, 1995

Related U.S. Application Data

[63] Continuation-in-part of Ser. No. 228,703, Apr. 15, 1994, abandoned.

[51] Int. Cl.[6] .................. A23L 1/237; A23L 1/221; A23L 1/23
[52] U.S. Cl. .................. 426/649; 426/650; 426/656; 426/648; 426/576; 426/657
[58] Field of Search .................. 426/649, 650, 426/656, 648, 576, 657

[56] References Cited

U.S. PATENT DOCUMENTS

| 2,471,144 | 1/1949 | Davy . |
|---|---|---|
| 2,601,112 | 6/1952 | Freedman . |
| 3,391,001 | 7/1968 | Sair . |
| 3,782,974 | 1/1974 | Lontz et al. . |
| 3,857,966 | 12/1974 | Feldman et al. . |
| 4,243,691 | 1/1981 | Mohlerkamp, Jr. et al. . |
| 4,340,614 | 7/1982 | Pich et al. . |
| 4,451,494 | 5/1984 | Roan, III . |
| 4,482,574 | 11/1984 | Lee . |
| 4,595,594 | 6/1986 | Lee et al. . |
| 4,798,736 | 1/1989 | Belohlawek . |
| 4,931,305 | 6/1990 | Karpparen et al. . |
| 4,997,672 | 3/1991 | DeSimone et al. . |
| 5,000,977 | 3/1991 | Marggrander et al. . |
| 5,102,987 | 4/1992 | Comet et al. . |
| 5,213,838 | 5/1993 | Sheikh . |
| 5,260,091 | 11/1993 | Locke et al. . |
| 5,288,510 | 2/1994 | Gregory et al. . |
| 5,370,882 | 12/1994 | Lee et al. . |

FOREIGN PATENT DOCUMENTS

0087247A2  8/1983  European Pat. Off. .

OTHER PUBLICATIONS

USDA Nutrient Database for Standard Reference Gelatin & Egg. Abstracted from Nutrien Data Lab. Agri. Ees. Service, (1997).
Derwent Abstract No. 86–227530 (1986).
Derwent Abstract No. 87–217628 (1987).

*Primary Examiner*—Donald E. Czaja
*Assistant Examiner*—Lhoon R. Koh
*Attorney, Agent, or Firm*—Vogt & O'Donnell, LLP

[57] ABSTRACT

The salty taste of a food or beverage is enhanced by adding to the food or beverage a dehydrated composition containing from about 15% to about 65% by weight of an ammonium salt and from about 35% to about 85% by weight of a proteolyzed protein. The dehydrated composition contains from about 0.2% to about 3% free lysine and from about 0.2% to about 3% free arginine.

28 Claims, No Drawings

COMPOSITIONS TO ENHANCE TASTE OF SALT USED IN REDUCED AMOUNTS

CROSS-REFERENCE TO RELATED APPLICATION

This application is a continuation-in-part of application Ser. No. 08/228,103, filed Apr. 15, 1994 now abandoned.

BACKGROUND OF THE INVENTION

The present invention relates to salt and flavor enhanced foods, more particularly to food compositions containing ammonium salts and modified protein as salt and flavor enhancers.

Excessive dietary sodium intake, the primary source of which is sodium chloride or table salt in foods, has long been suspected as a source of a number of health problems. Consequently, a reduction in sodium consumption would imply benefits for the health of most people. However, the inclusion of sodium chloride in the diet contributes a good deal to the palatability of foods, and food without salt is perceived to be tasteless, flat and unpalatable.

One approach for reducing sodium chloride intake has been the use of salt substitutes, the most popular of which are potassium chloride, ammonium chloride and mixtures thereof. Such salt substitutes suffer from a number of disadvantages, however, including sour off-tastes or bitter flavors, and taste perception different from and less than sodium chloride. Typically, therefore, a number of other components have been combined with such salt substitutes to mask the bitterness imparted thereby. For example, potassium chloride has been combined with calcium and magnesium formate and citrate salts, sugar, choline citrate, hydrolyzed animal protein, and lactate or lactic salt.

Another procedure which has been suggested for reducing sodium intake is to incorporate salt taste enhancers in foods and beverages. Such compounds do not replace sodium chloride, but rather enhance the taste of sodium chloride present in foods and beverages, thereby enabling the sodium chloride content to be reduced without adversely affecting the desired salty taste. Examples of salt taste enhancers which have been proposed include cationic surfactants, bretylium tosylate, certain polypeptides and encapsulated ammonium salts.

SUMMARY OF THE INVENTION

We have found that a salt taste-enhancing composition may be conveniently prepared by enzymatically hydrolyzing a protein substantially in the absence of added sodium, such that the resulting hydrolysate contains peptides and free amino acids, particularly free lysine and free arginine, in combination with an ammonium salt. When the hydrolysate is dehydrated and added to a food or beverage containing less than a normal amount of sodium chloride, it enhances the salty taste and, in some cases, the flavor of the food or beverage. Since the dehydrated composition contains significant amounts of assimilable dietary protein, it has nutritional value as well as salt taste-enhancing properties. And since the protein is enzymatically hydrolyzed substantially in the absence of added sodium, the amounts of sodium present in the dehydrated composition is controlled, thereby facilitating the use of the composition to enhance the salt taste of a wide variety of foods and beverages.

In particular, the present invention provides a process for preparing a dehydrated salt taste-enhancing composition comprising enzymatically hydrolyzing a protein in an aqueous reaction medium substantially free of added sodium, for a time sufficient to generate peptides and free amino acids, including free lysine and free arginine; adding to the reaction medium an ammonium salt, or an acid or alkalai which forms an ammonium salt with a complementary acid or alkalai; and dehydrating the aqueous reaction medium to obtain a dehydrated composition.

The present invention also provides a dehydrated salt taste-enhancing composition comprising from about 5% to about 65% by weight of an ammonium salt and from about 35% to about 95% by weight of a proteolyzed protein containing free arginine and free lysine. The dehydrated composition comprises from about 0.2% to about 3.0% by weight free lysine and from about 0.2% to about 3.0% by weight free arginine.

The present invention also provides a dehydrated salt extender composition, comprising the above-described salt taste-enhancing composition in combination with granular sodium chloride. The salt taste-enhancing composition and sodium chloride may be combined in a ratio, by weight, of from about 0.5 to 2:1.

The present invention also provides a process for enhancing the salty taste of a food or beverage containing a reduced amount of sodium chloride, comprising adding a salt taste-enhancing amount of the above-described salt taste-enhancing composition to a food or beverage which contains at least about 0.2% by weight sodium chloride. The present invention also provides a process for salting a food or beverage with a reduced amount of salt, comprising adding a salt taste-imparting amount of the above-described salt extender composition to a food or beverage.

DETAILED DESCRIPTION OF THE INVENTION

AS noted above, the salt taste-enhancing composition of the invention is dehydrated and has two essential components, i.e., an ammonium salt and a proteolyzed protein containing free arginine and free lysine.

As used herein, "dehydrated" is intended to mean that the substance or composition has a moisture content such that it is microbiologically stable upon storage at about 21° C., such as in a sealed container which is substantially impervious to moisture. In particular, the dehydrated composition should be substantially free of free water and/or have a water activity (i.e., $a_w$, water vapor pressure of the composition compared with the vapor pressure of water measured at the same temperature), of below 0.4, preferably below 0.3, and more preferably below 0.2. In general, the composition should have a moisture content on the order of less than 5% by weight, based upon the weight of the composition, preferably less than 3% by weight.

As used herein, "proteolyzed protein" is intended to mean all proteinaceous matter resulting from or present following proteolytic hydrolysis of a protein source. It includes free amino acids, small peptides, i.e., up to about 20 amino acid residues, polypeptides, and unmodified protein. As used herein, free amino acid is intended to mean discrete amino acids or salts thereof, including lysine, arginine and other free amino acids evolved during proteolysis.

The relative proportions of ammonium salt and proteolyzed protein in the dehydrated salt taste-enhancing composition of the invention may be adjusted, based upon the particular ammonium salt and protein used. The amounts of free arginine and free lysine in the composition remains constant, however, namely from about 0.2% to about 3.0% by weight. Preferably, the composition comprises from about 0.2% to about 5.0% by weight free glutamic acid, which imparts flavor.

The dehydrated salt taste-enhancing composition of the invention may also include minor amounts of other food-safe components, which may be added before, during or after proteolysis of the protein, or which may be evolved or generated during proteolysis and subsequent concentration and dehydration steps. The composition may thus contain ash, fibers, minerals, enzymes, etc. Preferably, the composition contains less than about 1% by weight sodium.

Suitable ammonium salts provided in the salt taste-enhancing composition of the invention include ammonium citrate, ammonium acetate, ammonium chloride, ammonium lactate, ammonium tartarate, ammonium fumarate, ammonium adipate, ammonium maleate, ammonium succinate and ammonium gluconate. The preferred ammonium salt is ammonium phosphate.

Suitable protein sources for the proteolyzed protein provided in the salt taste-enhancing composition of the invention include egg white, gelatin, soy protein, wheat protein, corn protein, fish protein, milk protein and meat protein. The protein may be fresh, frozen or dehydrated. Upon proteolysis, the protein yields free amino acids, including free arginine and free lysine, together with peptides of diverse length, varying with the protein source and protease used.

A preferred salt taste-enhancing composition of the invention combines ammonium phosphate and proteolyzed egg white, wherein the ammonium phosphate comprises from about 15% to about 45% by weight of the composition, preferably from about 17% to about 40% by weight, and the proteolyzed egg white comprises from about 55% to about 85% by weight, preferably from about 60% to about 83% by weight. In another preferred embodiment, ammonium phosphate is combined with proteolyzed gelatin, wherein the ammonium phosphate comprises from about 5% to about 20% by weight of the composition, preferably from about 7% to about 11% by weight, and the proteolyzed gelatin comprises from about 80% to about 95% by weight, preferably from about 89% to about 93% by weight.

Other suitable formulations of the salt taste-enhancing composition of the invention are illustrated in the Table below, where percentages indicated are by weight, based on the weight of the composition.

| AMMONIUM SALT | % | PROTEOLYZED PROTEIN | % |
| --- | --- | --- | --- |
| AMMONIUM CITRATE | 30–58 | EGG WHITE | 42–70 |
| AMMONIUM ACETATE | 30–58 | EGG WHITE | 42–70 |
| AMMONIUM LACTATE | 25–65 | EGG WHITE | 35–75 |
| AMMONIUM TARTARATE | 15–45 | EGG WHITE | 55–85 |
| AMMONIUM CITRATE | 7–15 | GELATIN | 85–93 |
| AMMONIUM ACETATE | 7–15 | GELATIN | 85–93 |
| AMMONIUM LACTATE | 6–17 | GELATIN | 83–94 |
| AMMONIUM TARTARATE | 6–17 | GELATIN | 83–94 |
| AMMONIUM PHOSPHATE | 10–40 | SOY | 60–90 |
| AMMONIUM CITRATE | 20–50 | SOY | 50–80 |
| AMMONIUM ACETATE | 20–50 | SOY | 50–80 |
| AMMONIUM LACTATE | 6–22 | SOY | 78–94 |
| AMMONIUM TARTARATE | 6–22 | SOY | 78–94 |

It is to be understood that the salt taste-enhancing composition of the invention is not a salt substitute, in that it does not completely replace sodium chloride in the food or beverage which is ultimately consumed. Rather, it is a salt taste enhancer and thus requires a minimum amount of sodium chloride in the food or beverage to be consumed, namely at least about 0.20% by weight, based upon the weight of the food or beverage.

The dehydrated salt taste-enhancing composition of the invention may be incorporated into a food or beverage to be consumed in any salt taste-enhancing amount. Although amounts of up to about 3% or more of the composition may be used, the amount used is generally from about 0.1% to about 0.7% by weight, based on the weight of the consumed food or beverage. Typically, the composition is added in an amount of from about 0.35% to about 0.50% by weight. The ratio by weight of the dehydrated composition and sodium chloride in the consumed food or beverage is typically 0.3 to 2.0:1.

Although not limited thereto, the dehydrated salt taste-enhancing composition of the invention is particularly well suited for use in the commercial/industrial food service setting, where it may be employed in the preparation of composite food products, for example. Preferably, the composition is packaged in a sealed container, e.g., envelope, pouch or jar, having printed instructions associated therewith (such as on a portion of the container or as an insert) for combining the dehydrated composition with another component to prepare a composite food product.

As noted above, granular sodium chloride may be combined with the salt taste-enhancing composition of the invention to provide the dehydrated salt extender composition of the invention, which may be used to salt foods which contain little or no salt. The salt taste-enhancing composition and sodium chloride may be combined in a ratio, by weight, of from about 0.5 to 2:1, more preferably from about 0.75 to 1.25:1.

For ease of portioning and incorporating the salt extender composition of the invention into a food or beverage, bulking agents known in the art, including starches, particularly corn starch and/or derivatives thereof, including dextrins, particularly maltodextrin and cyclodextrin, and the like, may be formulated in the composition as a carrier/diluent. Non-fat dry milk may also be used.

Although not limited thereto, the salt extender composition of the invention is particularly well suited for use in the domestic/household setting, where it may be employed to season foods during preparation or at the time of comsumption, i.e., at the stove or table. Thus, as with the salt taste-enhancing composition of the invention, the salt extender composition of the invention may be packaged in suitable containers or dispensers, e.g., shakers, which may be provided with instructions for measurement and/or use in combining with foods or beverages.

As noted above, the salt taste-enhancing compositions of the invention may be conveniently prepared from the proteolysis of a protein which, upon hydrolysis, yields peptides and free basic amino acids, particularly free lysine and free arginine. As also noted above, the enzymatic hydrolysis of the protein takes place in an aqueous reaction medium "substantially free of added sodium," which is intended to mean that no sodium or such minor amounts of sodium are added to the aqueous reaction medium so that, upon dehydration of the aqueous reaction medium, the dehydrated salt taste-enhancing composition contains less than about 1% by weight sodium. As would be understood, the amount of sodium which may be added to the aqueous reaction medium and fall within the stated limit will vary, depending upon the amount of sodium present in the protein starting material. Egg white, for example, naturally contains more sodium than gelatin, so less sodium can be added to the aqueous reaction medium in the case of proteolyzed egg white than in the case of proteolyzed gelatin.

Although the protein source may be enzymatically hydrolyzed in a single stage, under neutral, acid or alkaline conditions, the protein is preferably proteolyzed in two separate stages. In particular, the proteolysis may be carried out under (1) acid conditions and (2) neutral or alkaline conditions, sequentially and in any order. Between the first and second proteolysis steps, depending on the protease selected for the first stage, the pH is adjusted for the second proteolysis stage.

The degree of hydrolysis of the protein following proteolysis may be from about 10% to about 60%, preferably from about 20% to about 40%, as measured by the OPA method for measuring $\alpha$-amino group concentration. The concentration of free lysine and arginine may be determined, for example, by HPLC.

Conveniently, the protein source may be added to an aqueous solution of the protease, either in powder form or as an aqueous solution. Advantageously, the protein source and the protease are dissolved in water, for instance, by agitation. The concentration of the protein source in the aqueous solution may be from 5% to 40%, preferably from 10 to 30% and especially from 15% to 25% by weight, based on the weight of the solution. Conveniently, in the case of acid proteolysis, the pH of the solution of the protein and protease is adjusted to the desired value by acid addition after the dissolution of the protein source. In the case of neutral or alkaline proteolysis, the pH of the solution may be adjusted to the desired value by alkalai addition before, during or after dissolution of the protein source.

The acid proteolysis is conveniently carried out, for example, at a pH of from 1 to 6, preferably from 1.5 to 5 and especially from 2 to 4. The temperature at which the acid proteolysis is carried out may be from 0° C. to 65° C., preferably from 40° C. to 60° C. and especially from 45° C. to 55° C.

The adjustment of the pH of the aqueous reaction medium for the acid proteolysis may be effected by any suitable food acceptable acidulant, such as hydrochloric acid, acetic acid, lactic acid, citric acid or phosphoric acid.

Any protease suitable for use under acid conditions, and capable of generating free amino acids, particularly free lysine and free arginine, may be used for the acid proteolysis. Suitable enzymes include acid protease (Biocon or Amano), pepsin, bromelain and papain. The amount of protease used for the acid proteolysis may be from 0.005 to 4%, preferably from 0.02 to 1% and especially from 0.05 to 0.5% by weight based on the weight of the protein source.

The duration of the acid proteolysis may vary widely depending, for example, on the particular protease used, on the concentration of the protein and protease and on the temperature and pH. For example, the duration of the acid proteolysis may be from 2 to 48 hours or more, but typically the time ranges from 8 to 24 hours, and preferably from 12 to 20 hours.

The neutral or alkaline proteolysis is conveniently carried out at a pH of from 6 to 12, preferably from 6.5 to 9 and especially from 7 to 8.

Any protease suitable for use under neutral or alkaline conditions, and capable of generating free amino acids, particularly free lysine and free arginine, may be used for the neutral or alkaline proteolysis. Suitable enzymes include ALCALASE (Novo), PROTEASE-2A (Amano), NEUTRASE (Novo), PROZYME (Amano), trypsin (Novo) and pancreatic lipase (Solvay). Also suitable are aminopeptidases, including FLAVORZYME (Novo), PEPTIDASE-A (Amano) and DEBITRASE (Imperial Biotech). The amount of protease used for neutral or alkaline proteolysis may be from 0.005 to 4%, preferably from 0.02 to 1% and especially from 0.05 to 0.5% by weight, based on the weight of the protein source.

The temperature at which the neutral or alkaline proteolysis is carried out may be from 0° C. to 70°, preferably from 20° to 65° C. and especially from 50° to 60° C.

The duration of the neutral or alkaline proteolysis may vary widely depending, for example, on the particular protease used, on the concentration of the protein and protease and on the temperature and pH. For example, the duration of the neutral or alkaline proteolysis may be from 10 minutes to 24 hours or more, but typically the time ranges from 30 minutes to 6 hours and preferably from 1 to 4 hours.

Any suitable food acceptable (preferably non-sodium) alkalai, such as ammonium hydroxide, potassium hydroxide, potassium citrate and dipotassium phosphate, may be used to control the pH of the aqueous reaction medium during neutral or alkaline hydrolysis.

After the termination of both stages of the proteolysis, depending on the nature of the protein source, and depending on the order of the protease reactions, an acid or alkali may be added to the aqueous reaction medium containing the proteolyzed protein to produce an ammonium salt with a complementary acid or alkalai, thus adjusting the pH, e.g., to a pH of 5.5 to 7.5, preferably to a pH of 6.5 to 7.4. In addition, or alternatively, an ammonium salt may be added to the proteolyzed protein solution to increase the salt concentration, by adding the salt, or complementary acid and alkalai, to the aqueous proteolyzed protein solution, thus adjusting the pH from 4 to 9, preferably from 5 to 8 and especially from 6 to 7.

Salts other than ammonium salts may be formed in or added to the aqueous reaction medium. It should be understood, however, that in all cases, such additional salts should not be sodium salts, particularly not sodium chloride. Thus, suitable alkalai which may be added to the aqueous reaction medium are ammonium hydroxide, aqueous or gaseous ammonia, potassium hydroxide, potassium citrate or dipotassium phosphate. Suitable acids which may be added are hydrochloric acid, acetic acid, lactic acid, citric acid and phosphoric acid, although it is preferred not to employ hydrochloric acid. The addition of ammonium hydroxide and phosphoric acid, to form ammonium phosphate in situ, is particularly advantageous and preferred.

Conveniently, the aqueous reaction medium containing the ammonium salt and proteolyzed protein may be heated to inactivate the protease and, optionally, to pasteurize the solution, e.g., at a temperature from 70° to 120° C., preferably from 80° to 110° C., and especially from 90° to 100° C. The heating/pasteurization may be carried out for a period of from 3 to 30 minutes, preferably from 5 to 20 minutes, and especially from 10 to 15 minutes, by steam injection or heat exchanger, preferably a shell and tube or a plate and frame heat exchanger.

After pasteurization, the product is usually a liquid or slurry-like product containing undissolved solids. Although it may be used "as is" for salt taste-enhancing applications, the product is preferably concentrated and/or dried. If the product is dried, the drying is preferably carried out by spray drying. Advantageously, owing to the high protein concentration, the pasteurized product can be spray dried directly, i.e., without the use of a carrier such as maltodextrin. After drying, the product may be cooled and stored at room temperature in a sealed container for later use.

If it is desired to separate undissolved solids from the liquid portion of the product, the separation process may be carried out by filtration, in all its variants, and preferably by centrifugation, especially using a disc centrifugal clarifier or decanter. Although the liquid phase obtained after separation may be used as is, it is preferably concentrated, e.g., by vacuum evaporation, and/or dried, e.g., by spray drying with use of a suitable carrier, e.g., maltodextrin.

EXAMPLES

The following Examples further illustrate the present invention.

Example 1

1.7 kg of egg white are dissolved in 9.0 kg of water at ambient temperature and mixed at 150 rpm. 160 ml of 85% phosphoric acid having a specific gravity of 1.70 are added to adjust the pH to 3. 2.3 g of acid protease (Biocon) are added and the acidified mixture is stirred at 250 rpm at 50° C. for 16 hours in a fermenter. The proteolyzed product is transferred to a glass reactor and 1200 ml of 28–30% ammonium hydroxide having a specific gravity of 0.90 are added to adjust the pH to 9.6. 2.3 g of ALCALASE (Novo) are added and the alkaline mixture is stirred at 150 rpm at 58° C. for 2 hours in a glass reactor. A further 1000 ml of 85% phosphoric acid having a specific gravity of 1.70 are added to adjust the pH to 5.6 and the mixture is heated in hot water for 10 minutes at 121° C.

The heated solution is pre-filtered with a Buchner funnel (Whatman #54 filter paper) and then vacuum filtered to give a filtrate having a solids content of 24.24% by weight.

The liquid filtrate is then evaporated for 15 minutes under the following conditions:
Product initial temperature: 10° C.
Product final temperature: 37° C.
Vacuum: 635 mm Hg The solids content after evaporation is 45.46% by weight.

The evaporated product is then spray dried in a Niro Spray Drier under the following conditions:
Air pressure: 6 kg/cm$^2$
Air inlet temperature: 150° C.
Air outlet temperature: 90° C.
Product inlet temperature: 36° C.
Flow rate of product: set to obtain an outlet temperature of 90° C.

The final mass of the product is 1.57 kg and the amount of water evaporated is 2.210 kg.

The degree of hydrolysis is measured according to the OPA method of samples taken before enzyme addition and after spray drying. The final results are expressed as free amino groups per gram of powder.
Initial sample: $5.22 \times 10^{-4}$ mol of free amino groups per gram of powder
Final sample: $1.56 \times 10^{-3}$ mol of free amino groups per gram of powder The dehydrated composition contains approximately 40% by weight ammonium phosphate and approximately 60% by weight proteolyzed egg white. It contains approximately 0.4% by weight free lysine, approximately 0.56% by weight free arginine, and approximately 0.64% by weight free glutamic acid. It has a final moisture content of approximately 3%.

Example 2

2.25 kg of gelatin are dissolved in 11.270 kg of water at ambient temperature in a metal reactor. The pH of this solution is adjusted with ammonium hydroxide (28%) to 7.5 and the temperature adjusted to 50° C. by indirect heating with steam. Then, 4 g of the protease Neutrase (Novo) are added under continuous agitation at 200 rpm. The proteolysis is carried out for 4 hours at 50° C. under continuous addition of ammonium hydroxide to maintain the pH at 7.5. After 4 hours of proteolysis, the pH of the solution is adjusted to 2.5 with phosphoric acid (85%) and 3 g of acid protease (Biocon) are added. The acid proteolysis is carried out for 16 hours, at 200 rpm, 50° C. and continuous addition of phosphoric acid to maintain the pH between 2.5 and 3.0. After 16 hours reaction, the hydrolyzed gelatin solution is heated up to 90° C. for 15 minutes, to inactivate the proteases, cooled down to 50° C., and the pH adjusted to 7.0 with ammonium hydroxide. The total amounts of ammonium hydroxide and phosphoric acid used for pH adjustment are 120 ml and 220 ml, respectively.

The product of the proteolysis is spray dried under the following conditions:
Product Inlet Temperature: 50° C.
Product Outlet Temperature: 85° C.
Air Inlet Temperature: 140° C.
Air Outlet Temperature: 85° C.

The dehydrated composition contains approximately 10% by weight ammonium phosphate and approximately 90% by weight proteolyzed gelatin. It contains approximately 0.5% by weight free lysine, approximately 1.4% by weight free arginine, and approximately 1.7% by weight free glutamic acid. The final moisture content is approximately 2.0%.

Example 3

850 g of water, added to a glass reactor, are heated to 58° C. and the pH adjusted to 3.0 with phosphoric acid. To this solution 3.0 g of acid protease (Biocon) are added under agitation (280 rpm). After 5 minutes of mixing, 220 g of soy protein are added and the proteolysis carried out for 5 hours at 57° C., 200 rpm and continuous addition of phosphoric acid to maintain the pH within the range 2.5–3.0. After 5 hours of proteolysis, ammonium hydroxide is added to adjust the pH to 7.0, the temperature falls to 50° C. and 3 g of PROTEASE-2A (Amano) are added under mixing. The proteolysis with PROTEASE-2A is carried out for 8 hours at 50° C., with continuous addition of ammonium hydroxide to maintain the pH within the range 6.5–7.3. After 8 hours of reaction, the proteolyzed soy protein is pasteurized at 100° C. for 10 minutes, cooled down to 50° C. and filtered with filter aid. Zeolite is used as filter aid at a ratio of 30% of final solids in hydrolyzed product.

The liquid obtained after filtration is spray dried under the following conditions:
Product Inlet Temperature: 50° C.
Product Outlet Temperature: 85° C.
Air Inlet Temperature: 140° C.
Air Outlet Temperature: 85° C.

The final amount of ammonium hydroxide and phosphoric acid used are 40 ml and 30 ml, respectively.

The dehydrated composition has a moisture content of approximately 2.0%. It contains approximately 13% by weight ammonium phosphate and approximately 87% by weight proteolyzed soy protein. It contains approximately 1.1% by weight free lysine, approximately 1.3% by weight free arginine, and approximately 3.0% by weight free glutamic acid.

Example 4

A typical low-cost cheese sauce contains approximately 1.6% by weight sodium chloride. In order to demonstrate the effectiveness of the salt taste enhancer composition of the present invention, a comparable low-cost cheese sauce is formulated containing 0.5% sodium chloride, and is used as a control. To one aliquot of this control cheese sauce is added 0.25% by weight of the spray dried proteolyzed egg white prepared in Example 1, in the amounts indicated. The control cheese sauce and the sauce to which the salt enhancer is added are then evaluated by a sensory panel consisting of eight trained judges who are of the opinion that the proteolyzed egg white significantly amplifies the sodium chloride taste.

Various modifications of the compositions and processes of the present invention may be made without departing from the spirit and scope of the foregoing disclosure. Unless otherwise stated, the inventions may be carried out and embodied in the absence of elements, constituent composition components and/or process steps and/or parameters not specifically disclosed or excluded herein.

We claim:

1. A composition for enhancing a taste provided by salt in foods and beverages comprising, by weight based upon composition weight:
   dehydrated proteolyzed protein selected from the group consisting of proteolyzed egg white and proteolyzed gelatin in an amount of from 42% to about 95% including, based upon the composition weight, from about 0.2% to about 3% free lysine and from about 0.2% to about 3% free arginine; and
   ammonium salt in an amount of from about 5% to 58%.

2. A composition according to claim 1 wherein the ammonium salt comprises ammonium phosphate.

3. A composition according to claim 1 wherein the proteolyzed protein includes, based upon the composition weight, from about 0.2% to about 5% free glutamic acid.

4. A composition according to claim 1 wherein the composition comprises less than 1% sodium.

5. A composition according to claim 1 wherein the proteolyzed protein comprises proteolyzed egg white in an amount of from about 55% to about 85%.

6. A composition according to claim 5 wherein the ammonium salt comprises ammonium phosphate and is in an amount of from about 15% to about 45%.

7. A composition according to claim 1 wherein the proteolyzed protein is proteolyzed gelatin in an amount of from about 80% to about 95%.

8. A composition according to claim 7 wherein the ammonium salt comprises ammonium phosphate and is in an amount of from about 5% to about 20%.

9. A composition according to claim 1 further comprising sodium chloride in a ratio by weight so that the ratio of the proteolyzed protein and ammonium salt to the sodium chloride is from about 0.5:1 to 2:1.

10. A salt-extender product comprising:
    granular sodium chloride; and
    a composition comprising by weight:
      dehydrated proteolyzed protein selected from the group consisting of proteolyzed egg white and proteolyzed gelatin in an amount of from 42% to about 95% including, based upon the composition weight, from about 0.2% to about 3% free lysine and from about 0.2% to about 3% free arginine; and
      ammonium salt in an amount of from 5% to 58%; and
    wherein a ratio by weight of the protolyzed protein and ammonium salt composition to the sodium chloride is from 0.5:1 to 2:1.

11. A composition according to claim 10 wherein the ammonium salt comprises ammonium phosphate.

12. A composition according to claim 10 wherein the proteolyzed protein includes, based upon the composition weight, from about 0.2% to about 5% free glutamic acid.

13. A composition according to claim 10 wherein the proteolyzed protein and ammonium salt composition comprises less than 1% sodium.

14. A composition according to claim 10 wherein the proteolyzed protein comprises proteolyzed egg white in an amount of from about 55% to about 85%.

15. A composition according to claim 14 wherein the ammonium salt comprises ammonium phosphate and is in an amount of from about 15% to about 45%.

16. A composition according to claim 10 wherein the proteolyzed protein is proteolyzed gelatin in an amount of from about 80% to about 95%.

17. A composition according to claim 16 wherein the ammonium salt comprises ammonium phosphate and is in an amount of from about 5% to about 20%.

18. A process for enhancing the salty taste of a food or beverage, which comprises at least about 0.2% sodium chloride, comprising adding to the food or beverage an amount of a composition comprising by weight:
    dehydrated proteolyzed protein selected from the group consisting of proteolyzed egg white and proteolyzed gelatin in an amount of from 42% to about 95% including, based upon the composition weight, from about 0.2% to about 3% free lysine and from about 0.2% to about 3% free arginine; and
    ammonium salt in an amount of from about 5% to 58%.

19. A process according to claim 18 wherein the proteolyzed protein is proteolyzed egg white in an amount of from about 55% to about 85% and the ammonium salt comprises ammonium phosphate and is, in an amount of from about 15% to about 45%.

20. A process according to claim 18 wherein the proteolyzed protein is proteolyzed gelatin in an amount of from about 80% to about 95% and the ammonium salt comprises ammonium phosphate and is in a amount of from about 5% to about 20%.

21. A process of salting a food or beverage comprising adding to the food or beverage an amount of a salt extender product comprising by weight:
    dehydrated proteolyzed protein selected from the group consisting of proteolyzed egg white and proteolyzed gelatin in an amount of from 42% to about 95% including, based upon the composition weight, from about 0.2% to about 3% free lysine and from about 0.2% to about 3% free arginine; and
    ammonium salt in an amount of from about 5% to 58%.

22. A process according to claim 21 wherein the proteolyzed protein is proteolyzed egg white in an amount of from about 55% to about 85% and the ammonium salt comprises ammonium phosphate and is in an amount of from about 15% to about 45%.

23. A process according to claim 21 wherein the proteolyzed protein is proteolyzed gelatin in an amount of from about 80% to about 95% and the ammonium salt comprises ammonium phosphate and is in a amount of from about 5% to about 20%.

24. A process for obtaining a product for enhancing taste provided by salt comprising enzymatically hydrolyzing protein contained in a protein-containing reaction medium in two stages, wherein the protein is selected from the group consisting of egg white and gelatin, wherein a pH-adjusting substance comprising a substance selected from the group consisting of phosphoric acid and ammonium hydroxide is added to the reaction medium for controlling reaction medium pH so that a pH of the reaction medium of each stage differs and wherein an enzyme for hydrolyzing the protein in a first stage differs from an enzyme for hydrolyzing the protein in a second stage, and collecting a proteolyzed protein product and dehydrating the product to obtain a dehydrated product and so that the dehydrated product comprises by weight (a) dehdyrated proteolyzed protein in an amount of from 42% to about 95% including, based upon the product weight, from about 0.2% to about 3% free lysine and from about 0.2% to about 3% free arginine and (b) ammonium salt which comprises ammonium phosphate and which is in an amount of from about 5% to 58%.

25. A process according to claim 24 wherein the proteolyzed product collected is a filtrate.

26. A process according to claim 24 wherein the proteolyzed product collected is the hydrolyzed reaction medium.

27. A process according to claim 24 wherein the proteolyzed protein is proteolyzed egg white in an amount of from about 55% to about 85% and the ammonium salt comprises ammonium phosphate and is in an amount of from about 15% to about 45%.

28. A process according to claim 24 wherein the proteolyzed protein is proteolyzed gelatin in an amount of from about 80% to about 95% and the ammonium salt comprises ammonium phosphate and is in a amount of from about 5% to about 20%.

* * * * *

UNITED STATES PATENT AND TRADEMARK OFFICE
CERTIFICATE OF CORRECTION

PATENT NO. : 5,711,985
DATED : January 27, 1998
INVENTOR(S) : Arturo GUERRERO, et al.

It is certified that error appears in the above-indentified patent and that said Letters Patent is hereby corrected as shown below:

On the title page, left column, under the heading "Related U.S. Application Data", delete "228,703" and insert therefor -- 228,103 --.

Signed and Sealed this

Twenty-fifth Day of August, 1998

Attest:

BRUCE LEHMAN

*Attesting Officer*      *Commissioner of Patents and Trademarks*